United States Patent [19]
Euteneuer et al.

[11] Patent Number: 5,989,280
[45] Date of Patent: Nov. 23, 1999

[54] STENT DELIVERY APPARATUS AND METHOD

[75] Inventors: Charles L. Euteneuer, St. Michael; Phlayne M. Fraser, Eagan; Paul H. Burmeister, Maple Grove; Dean A. Peterson; Andrew W. Buirge, both of Minneapolis; Susan M. Shoemaker, Elk River, all of Minn.

[73] Assignee: Scimed Lifesystems, Inc, Maple Grove, Minn.

[21] Appl. No.: 08/633,726

[22] PCT Filed: Oct. 20, 1994

[86] PCT No.: PCT/US94/12050

§ 371 Date: Jun. 18, 1997

§ 102(e) Date: Jun. 18, 1997

[87] PCT Pub. No.: WO95/11055

PCT Pub. Date: Apr. 27, 1995

Related U.S. Application Data

[63] Continuation-in-part of application No. 08/141,269, Oct. 22, 1993, Pat. No. 5,571,135, and a continuation-in-part of application No. 08/245,919, May 19, 1994, Pat. No. 5,445,646.

[51] Int. Cl.$^6$ ................................................. A61M 29/00
[52] U.S. Cl. .................................. 606/198; 623/1; 623/12
[58] Field of Search ................................ 606/1, 108, 192, 606/194, 195, 198, 200; 623/1, 23; 604/96

[56] References Cited

U.S. PATENT DOCUMENTS

| | | |
|---|---|---|
| 3,911,927 | 10/1975 | Rich et al. . |
| 4,328,811 | 5/1982 | Fogarty . |
| 4,572,186 | 2/1986 | Gould et al. . |
| 4,606,347 | 8/1986 | Fogarty et al. . |
| 4,655,771 | 4/1987 | Wallsten . |
| 4,665,918 | 5/1987 | Garza et al. . |
| 4,681,110 | 7/1987 | Wiktor . |
| 4,699,611 | 10/1987 | Bowden . |
| 4,732,152 | 3/1988 | Wallsten . |
| 4,733,665 | 3/1988 | Palmaz . |
| 4,830,003 | 5/1989 | Wolff et al. . |
| 4,848,343 | 7/1989 | Wallsten et al. . |
| 4,863,440 | 9/1989 | Chin . |
| 4,875,480 | 10/1989 | Imbert . |
| 4,950,227 | 8/1990 | Savin . |
| 4,954,126 | 9/1990 | Wallsten . |
| 4,990,138 | 2/1991 | Bacich et al. . |
| 5,026,377 | 6/1991 | Burton et al. . |
| 5,061,275 | 10/1991 | Wallsten et al. . |
| 5,064,435 | 11/1991 | Porter . |
| 5,071,407 | 12/1991 | Termin et al. . |
| 5,074,845 | 12/1991 | Miraki et al. . |
| 5,078,720 | 1/1992 | Burton et al. . |
| 5,158,548 | 10/1992 | Lau et al. . |
| 5,192,297 | 3/1993 | Hull . |
| 5,201,757 | 4/1993 | Heyn et al. . |
| 5,234,457 | 8/1993 | Andersen . |
| 5,242,399 | 9/1993 | Lau et al. . |
| 5,261,878 | 11/1993 | Galindo . |
| 5,306,294 | 4/1994 | Winston et al. . |
| 5,344,426 | 9/1994 | Lau et al. . |
| 5,360,401 | 11/1994 | Turnland . |

*Primary Examiner*—Michael Buiz
*Assistant Examiner*—William Lewis
*Attorney, Agent, or Firm*—Vidas Arrett & Steinkraus, P.A.

[57] ABSTRACT

A delivery system for implantation of a self-expanding stent in a vessel is consists of an elongate flexible catheter for delivering a self-expanding stent to a predetermined location in a vessel. The stent surrounds the flexible catheter near its distal end and is held in a delivery configuration where the stent has a reduced radius along its entire axial length by a stent retaining and release means. The stent retaining and release means is a single layer sheath retaining sleeve means for retaining the stent in its delivery configuration attached to a slipping sleeve means for releasing the stent to self-expand. A balloon may optionally be used to seat the stent in the vessel after self-expansion. The stent may also optionally be retained by water soluble or swelling bands.

16 Claims, 11 Drawing Sheets

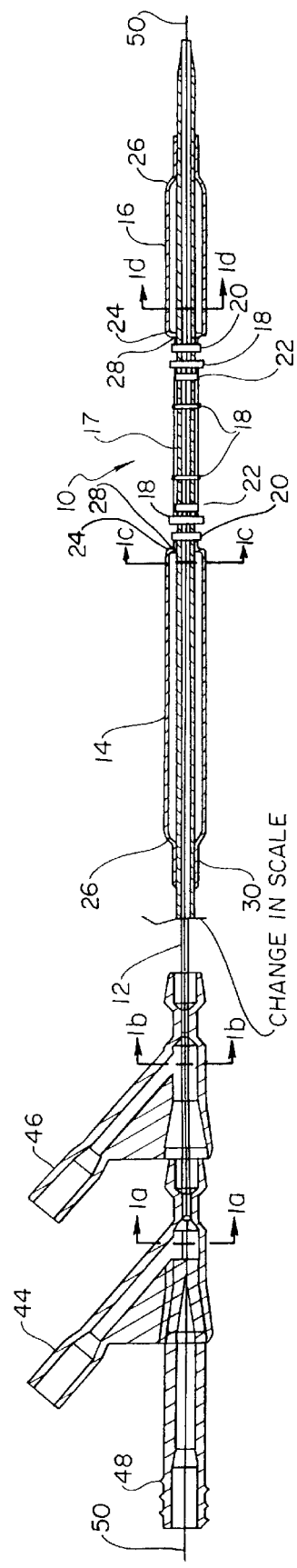
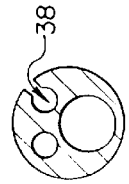
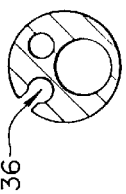
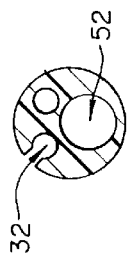

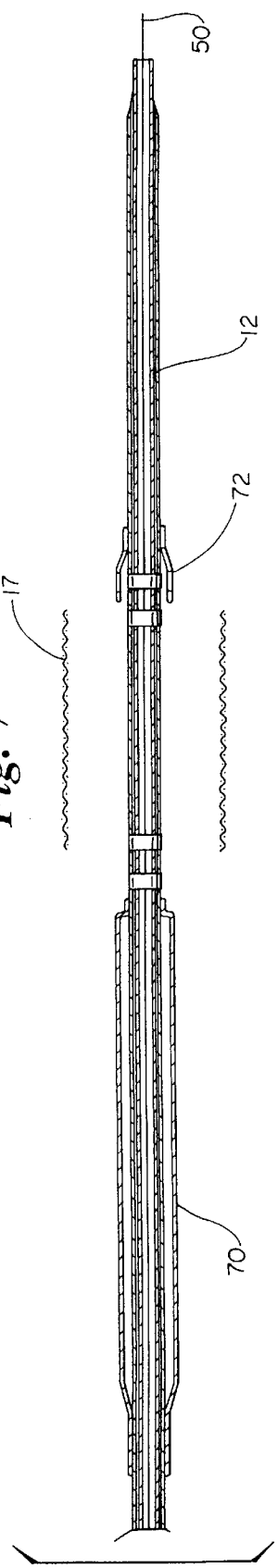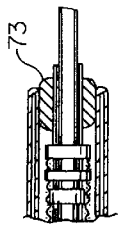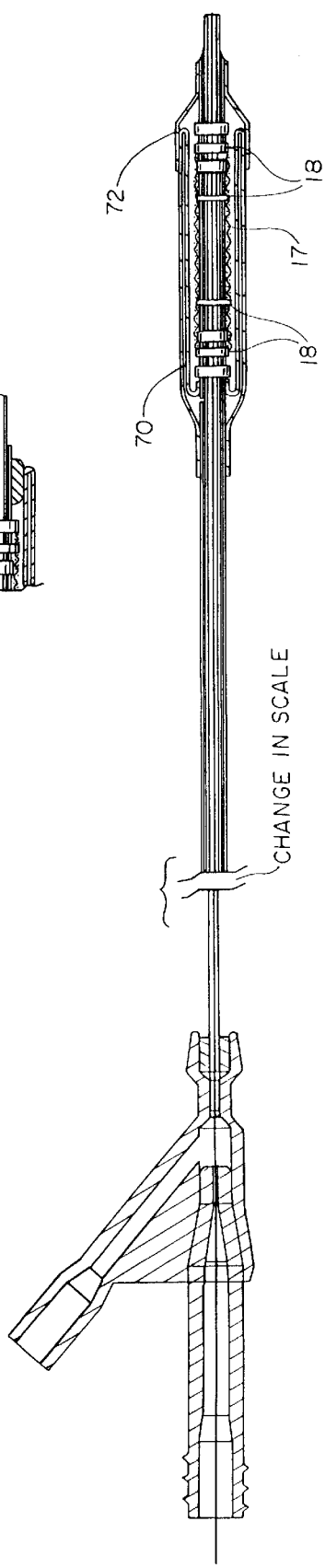
Fig. 7
Fig. 8a
Fig. 8

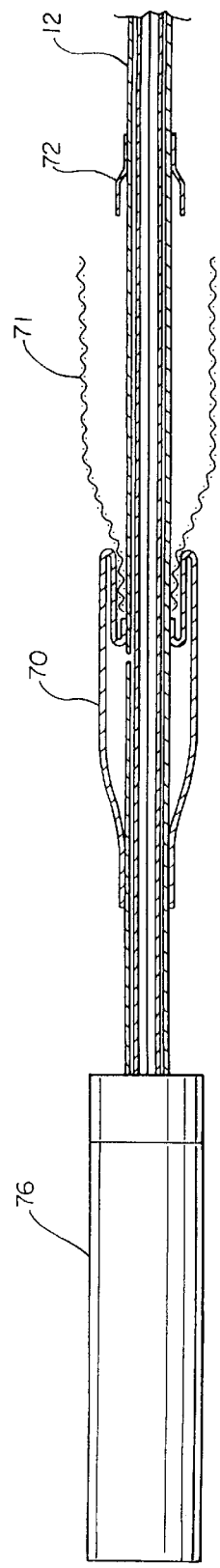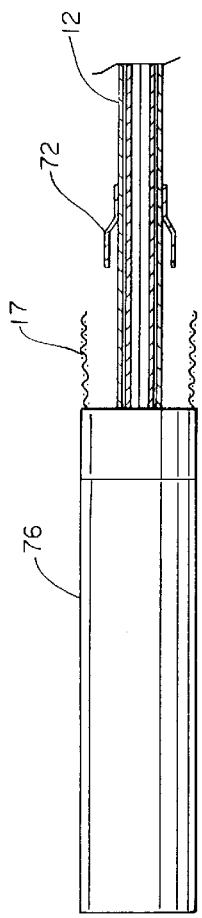
Fig. 10a
Fig. 10b

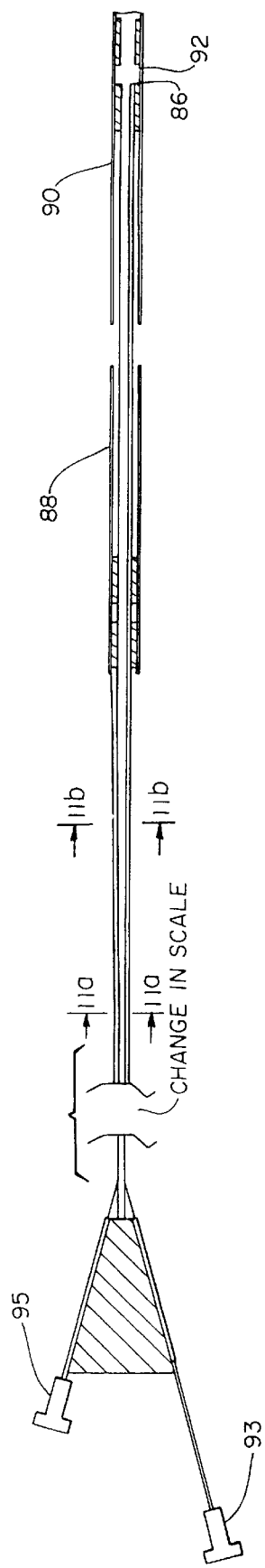
Fig. 11
Fig. 11b
Fig. 11a

STENT DELIVERY APPARATUS AND METHOD

CROSS REFERENCE TO RELATED APPLICATIONS

This application is a continuation-in-part of application No. 08/141,269, filed Oct. 22, 1993 and a continuation-in-part of application No. 08/245,919, filed May 19, 1994, now U.S. Pat. No. 5,445,646, now U.S. Pat. No. 5,445,646.

BACKGROUND OF THE INVENTION

1. Field of the Invention

The present invention relates to a delivery system and method for delivering and deploying a stent. More specifically, the invention relates to a delivery system and method for delivering and deploying a self-expanding stent in a body lumen.

2. Description of the Related Art

Stents and delivery systems for deploying stents are a highly developed and well known field of medical technology. Stents have many well known uses and applications. A stent is a prosthesis which is generally tubular and which is expanded radially in a vessel or lumen to maintain its patency. Stents are widely used in body vessels, body canals, ducts or other body lumens.

The preferred present stent delivery apparatus and method utilizes a self-expanding stent, which is well known in the art. A well known self-expanding stent is the woven braided stent disclosed in U.S. Pat. Nos. 4,655,771 (Wallsten); 4,954,126 (Wallsten) and 5,061,275 (Wallsten), although any type of self-expanding stent may be deployed using the inventive delivery system and method. The delivery system of the present invention may also be used to deliver a balloon expanded stent and may also deliver stent grafts, which are well known in the art.

The delivery systems for stents are generally comprised of catheters with the stent axially surrounding the distal end of the catheter. It is highly desirable to keep the profile of the catheter as small as possible. Therefore, self-expanding stents are generally confined in a reduced radius for delivery to the deployment site. Once the stent is deployed the catheter is removed, leaving the stent implanted at the desired location to keep the vessel walls from closing.

A variety of techniques have been developed for holding a self-expanding stent in its reduced configuration while moving the distal end of the catheter to the deployment site. For example, in U.S. Pat. No. 4,655,771 (Wallsten), gripping members at either end of the stent hold the stent in an axially-elongated position, which causes the stent to take a reduced radius delivery configuration.

Another common technique for maintaining the self-expanding stent in a reduced radius delivery configuration is using a sheath which surrounds the stent and compresses it around the catheter. This technique is disclosed in U.S. Pat. No. 5,071,407 (Termin) and U.S. Pat. No. 5,064,435 (Porter), both of which use a silicon rubber sheath to compress the stent. A similar technique is disclosed in 5,026,377 (Burton) and 5,078,720 (Burton).

A variation on surrounding the stent with a sheath is disclosed in 4,732,152 (Wallsten); 4,848,343 (Wallsten) and 4,875,480 (Imbert), all of which disclose using a sleeve formed of a doubled-over section of membrane to compress and contain the stent.

U.S. Pat. No. 5,234,457 discloses using a sheath to surround a mesh stent of the type disclosed in U.S. Pat. No. 4,922,405. However, in this patent the sheath is not used to compress the stent, but is used to prevent fluid from accessing the stent. The stent is impregnated with a pure gelatin or other dissolvable material which, when cured, has sufficient strength to hold the stent in its reduced delivery configuration. Once the sheath is withdrawn, the stent is exposed to the body fluids which dissolve the gelatin, allowing the stent to self-expand. This reference also discloses using axial distribution of gelatins with different rates of thermal decomposition to control the physical profile of the stent as it expands. However, using an impregnated mesh stent adds several inconvenient manufacturing steps to the process of preparing the stent for implantation.

All of the methods for delivery of a stent discussed to this point involve releasing the stent starting from one end of the stent, except for Anderson 5,234,457 which can allow the stent to self-expand uniformly over its entire length. An improvement to this type of deployment is discussed in Heyn 5,201,757 which relates to medial deployment of a stent. Medial deployment of a stent releases the middle region of the stent before releasing either end of it. This tends to prevent stent movement during deployment.

All of the prior art methods of containing and deploying the self-expanding stent have several problems. First, many of the techniques require that movement of the entire sheath or exterior catheter take place to manipulate the distal end of the catheter and effect release of the stent. This can be seen in Wallsten 4,655,771 and Wallsten 4,954,126 in which tubular member 23 is moved forward from position 22 to position 30. In Termin 5,071,407 the sheath 32 is withdrawn proximally with respect to the stent. In Porter 5,064,435 the sheath 38 is withdrawn proximally with respect to the stent. Burton 5,026,377 also moves an outer sleeve backwards relative to the stent. In Wallsten 4,732,152; Wallsten 4,848, 343, and Imbert 4,875,480, a hose 5 is connected to a maneuvering tube 8 which runs the length of the catheter. Finally, in Heyn, finger grip 5, connected to section 58 causes outer catheter 20 and sleeve 24 to move proximally relative to the stent.

In all of the cases discussed above, movement occurs over the entire length of the catheter between the proximal end controlled by the physician and the distal end where the stent is released. This catheter movement in the vessel creates several problems. First, catheter movement can disturb or move the introducer sheath at the wound site where the catheter is inserted into the vessel. Secondly, in tortuous anatomy the added friction caused by rubbing the outer catheter against the vessel, as well as the added friction created between the inner/outer layer interface, can make deployment difficult. The translation of control movements from the proximal to the distal end is imprecise, jerky and in some instances impossible due to the increased friction caused by tortuosity. Thirdly, it can create trauma to the endothelium over the entire length of the catheter.

Another drawback to the prior art stent delivery systems discussed above is that requiring an extra sheath layer, sleeve layer or layered catheters (Heyn) increases the profile of the catheter, which is undesirable. The Heyn device described in U.S. Pat. No. 5,201,757 has a profile of 0.12 inches (3.048 mm). A reduction in profile of even 1F (French) is considered significant to those skilled in the art.

There remains a need in the art for a stent delivery system in which the catheter remains stationary in the vessel and movement is confined to the distal end of the catheter to avoid disturbing the introducer sheath, minimize trauma to the endothelium and allow for move easier and more accurate deployment in tortuous anatomy. Furthermore, there remains the need for a stent delivery catheter with a smaller profile than the prior art. There is also a need for an improved form of medial release.

SUMMARY OF THE INVENTION

The inventive stent delivery device includes a catheter with a stent held in a reduced delivery configuration for insertion and transport through a body lumen to a predetermined site for deployment of a stent, self-expanding stent, stent graft or the like. An embodiment utilizes a pair of slipping sleeves, each being a section of membrane folded over onto itself, which can either hold a self-expanding stent in the delivery configuration or form a watertight chamber for an enclosed holding means. When the slipping sleeves are used to form a watertight chamber, the stent is held in the delivery configuration by means of a tubular sleeve made of water soluble material; a plurality of bands made of water soluble material, swelling band(s) or other degradable material. A related embodiment can utilize only a single slipping sleeve in a non-medial release form.

An alternate embodiment of the stent delivery device includes separate lumens, each containing a teflon or hydrophilic coated wire extending to respective proximal and distal movable sleeves. The physician can individually control each sleeve by pulling on the wire connected to the proximal sleeve and/or pushing on the wire connected to the distal sleeve. A related embodiment can utilize only a single sleeve in a non-medial release form with a single wire.

In another embodiment of the stent delivery device, the separate lumens each contain proximal and distal pistons which are connected by teflon or hydrophilic coated wires extending to their respective proximal and distal sleeves. The lumens are connected by a fluid communication port, which is positioned such that the distal piston must move distally a predetermined distance before the fluid can access the port and flow into the proximal piston lumen, where it moves the proximal piston proximally. This causes a form of medial release in which the distal sleeve releases the distal end of the stent prior to release of the proximal end.

This application also discloses another embodiment called the single layer sheath stent delivery apparatus and method, which is an improvement of applicant's co-pending improved stent delivery apparatus and method application, filed Oct. 22, 1993 as Ser. No. 08/141,269. The entire contents of Ser. No. 08/141,269 filed Oct. 22, 1993 are hereby incorporated by reference.

The inventive single layer sheath stent delivery device embodiment includes a catheter with a stent held in a reduced delivery configuration for insertion and transport through a body lumen to a predetermined site for deployment of a stent, self-expanding stent, stent graft or the like. This embodiment utilizes a slipping sleeve, which is a section of membrane folded over onto itself, with a single layer sheath attached to the slipping sleeve which can hold a self-expanding stent in the delivery configuration. Fluid is inserted into the slipping sleeve through a fluid access port, and the pressure causes the slip seal end of the slipping sleeve to move axially away from the stent, retracting the single layer sheath attached to the slipping sleeve, thereby releasing the stent to self-expand. The invention will also deliver non self-expanding stents by placing the stent around an expandable balloon. Once the single layer sheath is retracted, the balloon is expanded to expand the stent.

An alternate embodiment of the single layer sheath stent delivery device provides medial release by using two single layer sheaths to retain the stent in the delivery configuration, each being attached to a slipping sleeve. Fluid pressure causes both slipping sleeves to move axially away from the stent, retracting their respective sections of single layer sheath to release the stent for self-expansion or balloon expansion.

Another alternate embodiment of the invention is a delivery system for implantation of a stent in a vessel, which includes an elongate flexible catheter having proximal and distal ends for delivering a self-expanding stent to a predetermined location in a vessel, the self-expanding stent having proximal and distal ends, the stent being in a delivery configuration where the stent has a reduced radius along its entire axial length and where the stent is held in its reduced delivery configuration by a swelling band stent retaining and release means for retaining the stent in the delivery configuration and for deploying the stent, comprised of at least one band made of a water swelling material, which holds the self-expanding stent in its delivery configuration against the outwardly urging force of the self-expanding stent until fluid swells the band, thereby releasing the stent to self-expand.

BRIEF DESCRIPTION OF THE DRAWINGS

A detailed description of the invention is hereafter described with specific reference being made to the drawings in which:

FIG. 1 is a side elevational section showing a stent deployment device with the slipping sleeves shown with the stent in the uncovered position, and with the stent held in a confined or reduced delivery configuration with a plurality of water soluble bands;

FIGS. 1a–1d are cross-sections;

FIG. 7 is a side elevational section showing yet another embodiment of a stent delivery device of the invention in an uncovered position;

FIG. 8 is a side elevational section of the distal end portion of the invention of FIG. 7 in the covered position;

FIG. 8A is a fragment of FIG. 8 showing an alternate embodiment to secure the slipping sleeve;

FIG. 10 is a side elevational section of the distal end portion of the invention showing the use of a guide catheter to retrieve a misplaced stent;

FIG. 11 is a side elevational section of a further embodiment of a stent delivery device according to the invention;

FIGS. 11a–11b are cross-sections;

DESCRIPTION OF THE PREFERRED EMBODIMENTS

Figure 2:
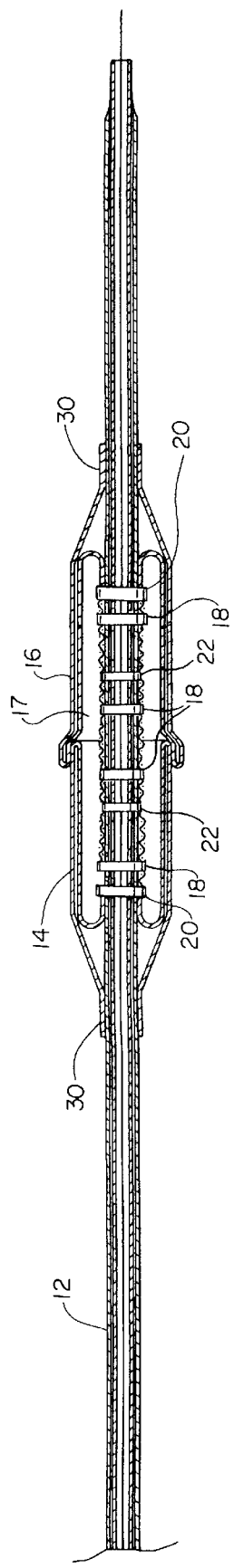
FIG. 2 is a side elevational section fragment of FIG. 2 showing the slipping sleeves of FIG. 1 in the covered position.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIG. 1 shows an embodiment of the inventive stent delivery apparatus, generally at 10, which is used to deliver the stent in a reduced radius delivery configuration to the deployment site in the body. Apparatus 10 includes an elongate flexible catheter 12, which in the this embodiment is extruded of a biocompatible and HPC (hydrophilic) compatible material such as a lubricous polyimide or polyethylene. Other suitable materials for catheter 12 include nylons, urethanes, polypropylene, and PEBAX materials which are compatible with silicone and/or hydrophilic coatings. It should be understood that while a hydrophilic compatible material is preferred, any biocompatible material may be used. The polyethylene or polypropylene, while not themselves hydrophilic can be coated with a hydrophilic material. Therefore, it can be seen that any biocompatible or HPC compatible material can be used to make catheter 12. As will be discussed below, the inventive stent delivery apparatus allows for the outside diameter of the catheter to be 5.3 French (F) (0.070 inches or 1.778 mm) or less using a 0.018 inch guidewire, which is a significant profile improvement over prior art such as Heyn 5,201,757 which discloses an outer diameter of 0.12 inches (3.048 mm).

The distal end portion of catheter 12 has a pair of slipping sleeves 14 and 16 which are used to form a waterproof chamber around a stent 17 carried by the catheter. Although this invention will be related primarily to using the inventive delivery apparatus for delivery of self-expanding stents, it should be understood that the inventive delivery apparatus may be used to deliver both self-expanding and non self-expanding stents, grafts and stent grafts. Stent 17 is a self-expanding stent, and in this embodiment is a so called woven braided stent of a type somewhat similar to those disclosed in Wallsten 4,655,771; Wallsten 4,954,126 and Wallsten 5,061,275. However, the disclosed stent delivery apparatus will deliver any type of self-expanding stent, such as for example, a stent made of any type of resilient metal or plastic, which would include a shape memory alloy type stent, such as a nitinol stent. Stent 17 is shown confined in its reduced radius delivery configuration by a plurality of water soluble bands 18, described further hereinbelow in FIGS. 3–6. Two pair of radiopaque marker bands 20 and 22 are bonded to catheter 12 with the marker bands of pair 20 being enlarged in diameter so as to additionally be used to aid in preventing stent 17 from moving axially while on the catheter. The use of radiographic or fluoroscopic imaging techniques to image the radiopaque marker bands to verify the correct positioning for stent deployment is well known in the art.

Slipping sleeves 14 and 16 are shown in FIG. 1 in the uncovered position. The slipping sleeves 14 and 16 are made of molded plastic and the preferred material is a polyolefin copolymer (POC) SURLYN™. Other materials such as fluoropolymers, noncompliant polyethylene terephthalate (PET); polyimide, nylon, polyethylene, PEBAX or the like may also be used. In this embodiment, slipping sleeves 14 and 16 are molded with an approximately 90° knee, shown at 24, and an approximately a 45° angle at 26. It has been found experimentally that the 90° knee at 24 and the 45° angle at 26 more easily allow the sleeve membrane material to roll over onto itself. Slipping sleeves 14 and 16 are slid over the catheter and bonded to the catheter at 28, as is well known in the art. The slipping seal 30 is formed a tolerance fit between the inner diameter of the seal 30 and the outer diameter of the catheter shaft.

A potential problem with a tolerance fit seal design is encountered when the slipping sleeve is restricted and a great deal of pressure is required to slid the sleeve. In this case, the pressure can become great enough to separate the seal and allow fluid to leak between the inner diameter of the seal 30 and the outer diameter of the catheter shaft. In seal design theory, it is a goal to have the integrity of the seal increase as pressure is increased. An embodiment that does this is shown in FIG. 2B by adding member 25. Member 25 is glued to the inner diameter of the sleeve and has a length protruding under the sleeve, and is therefore called an "L seal". As pressure is increased in the balloon, the L seal is held more tightly against the outer diameter of the catheter, decreasing the possibility of fluid leakage allowing pressure to build and slid the sleeve.

Manifolds 44 and 46 are used to introduce fluid into lumens 32 and 34 respectively. Manifold 48 is used to insert a guide wire 50 through central lumen 52, as is well known in the art. Reference numeral 54 shows a section of introducer sheath through which the catheter is inserted into a wound and into a vessel or body lumen.

One advantage the inventive stent delivery apparatus provides is that once the catheter has reached the deployment site, no further movement of the catheter is required to release the stent. All movement required to release the stent is internal to the catheter. By avoiding further movement of the catheter 12, the introducer sheath 54 is not disturbed or moved from its body introduction site, which reduces trauma to the entrance wound. Also, avoiding further movement of catheter 12 minimizes trauma to the endothelium, which is desirable. By avoiding external catheter movement to deploy the stent 17, the inventive delivery apparatus can be used to deliver stents in more tortuous anatomy as well as allow more precise and accurate control.

Referring now to FIG. 2, the distal end portion of catheter 12 is shown with slipping sleeves 14 and 16 forming a waterproof chamber around stent 17. Slipping sleeves 14 and 16 are formed of a doubled-over section of membrane caused by urging seals 30 of sleeves 14 and 16 axially toward each other. This causes the membranes to roll over from their position as seen in FIG. 1 onto themselves at knees 24 as is seen in FIG. 2. It can be seen that sleeves 14 and 16 slightly overlap to form a seal. Stent 17 confined to its reduced radius by bands 18 and positioned between marker bands 20 in the chamber formed by sleeves 14 and 16.

Figure 3:
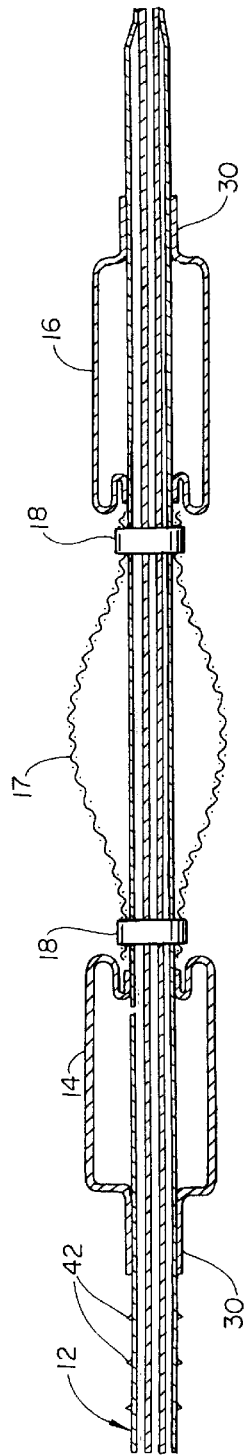
FIG. 3 is a side elevational section of the distal end portion of a deployment device showing the slipping sleeves of FIG. 2 retracted and with the middle bands dissolved.

FIG. 3 shows the apparatus of FIGS. 1 and 2 in mid-deployment, i.e. the two center bands being dissolved. Fluid has been introduced through manifolds 44 and 46 and into lumens 32 and 34 to enter sleeves 14 and 16. The chamber formed by the sealed end 28 and the slipping seal 30 of the sleeve is filled through inflation ports 36 and 38 of each sleeve, respectively. As the fluid pressure builds in sleeves 14 and 16, fluid is forced out through seal 30 causing seal 30 to slid away from the stent 17 along the catheter 12, thereby retracting sleeves 14 and 16 to expose or uncover stent 17 to body fluids.

The water soluble bands 18 are preferably a polyethyleneoxide (PEO), but can be polyvinylpryyolidone (PVP); polyvinyl alcohol (PVA); mannitol, complex carbohydrates or the like, and the composition of individual bands can be varied as desired. In FIG. 3, the bands surrounding the medial portion of stent 17 were constructed such that they dissolved faster than the outer bands 18, resulting in the medial release shown in FIG. 3. This can be accomplished by varying the molecular weights of the compositions, since the lower the molecular weight the faster the band 18 will dissolve. Varying the thickness or adding perforations (discussed below in connection with FIGS. 5 and 6) will also increase the rate of dissolution.

Figure 4:
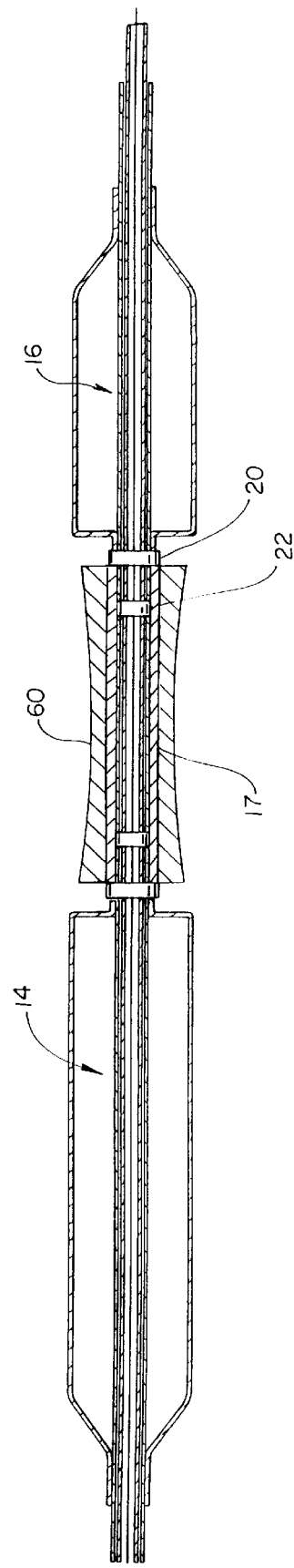
FIG. 4 is a showing similar to FIG. 3 illustrating a first alternate embodiment of the water soluble bands of the invention.
Figure 5:
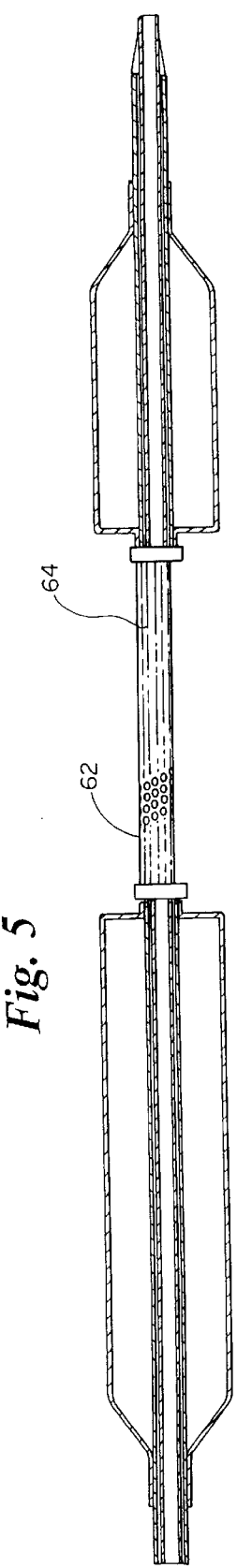
FIG. 5 is a showing similar to FIG. 3 illustrating a second alternate embodiment of the water soluble bands of the invention.

FIGS. 4 and 5 show alternate embodiments of water soluble bands 18. In FIG. 4, the plurality of bands axially spaced along stent 17 as shown in FIG. 2 have been replaced by a single tubular band 60. In the embodiment of tubular band 60 shown in FIG. 4, the band is thinner in the middle than at either end and will therefore dissolve faster in the middle, allowing medial deployment. It can be understood that the thickness of band 60 can be varied as desired to allow for a controlled release of stent 17 in any manner desired by the physician, such as releasing the stent starting from either the proximal or distal end or in other sequential deployments. It should also be understood that band 60 can be of the same thickness, but by varying the composition of predetermined sections of the band 60, those predetermined sections can be dissolved at a faster rate, allowing for a controlled release of stent 17.

FIG. 5 shows a tubular band 62 which has perforations 64 throughout. Perforations 64 are more dense in the middle section of band 62 than at either end section, thereby allowing the middle section of band 62 to dissolve faster, whether composition or thickness is varied or both. Again, the denseness of perforations 64 can be controlled throughout band 62 to allow for any type of sequential dissolution and self-expansion of stent 17, as desired.

An alternate embodiment to the use of water soluble bands 18, 60 or 62 is to utilize a swelling band or other degradable material which is attached to the catheter 12. This swelling band material can be complex carbohydrates, cellulose, crosslinked PVA/PVP, polyethylene/acrylic acid or the like. Self-expanding stent 17 is pressed into the swelling band material, which after curing, will hold stent 17 in its reduced radius delivery configuration. Retracting sleeves 14 and 16 exposes the swelling band material to body fluids, which will expand or swell, releasing the stent 17 to self-expand. Because the swelling band material is attached to the catheter 12, it will be withdrawn from the body along with the catheter. It should be understood that the composition of the swelling material could be varied to control the expansion of stent 17 as above.

Figure 6:
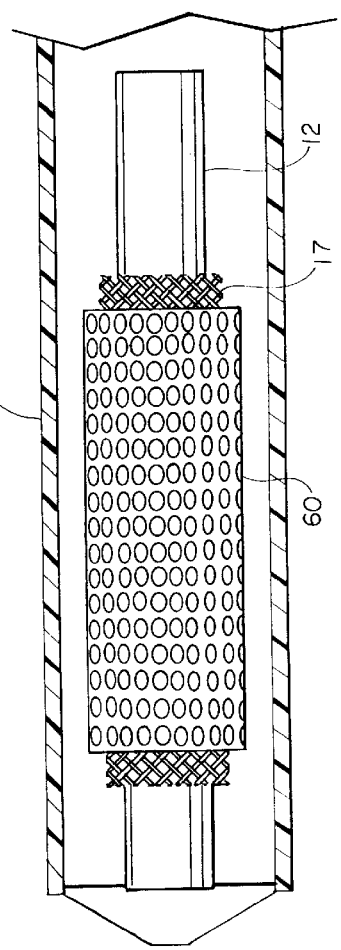
FIG. 6 is a side elevational section showing another embodiment of a stent delivery device according to the invention.

FIG. 6 shows another embodiment of the stent delivery device in which the sleeves 14 and 16 have been replaced by a retractable sheath 66. Retractable sheath 66 can be withdrawn using a wire as discussed below in connection with the push/pull sleeve and hydraulic sleeve embodiments. Retraction of sheath 66 allows body fluid to access and dissolve band 60. It should be understood that the variations of water soluble or swelling material described above can be used in connection with this embodiment.

One of the important features of the inventive stent delivery apparatus is that it allows the physician to deploy the stent in a variety of ways. For example the stent can be medially deployed, deployed starting from the distal end of the stent or deployed starting from the proximal end of the stent. With medial deployment, either the proximal or distal end of the stent can be released from its sleeve first or they can both be released at the same time, which provides maximum flexibility to the physician.

Figure 2A:
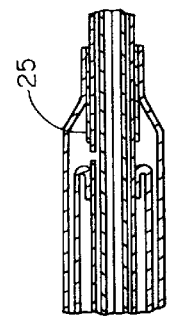
FIG. 2A is a fragment of FIG. 2 showing an alternate embodiment of the slipping sleeve inflation of FIG. 2.
Figure 2B:
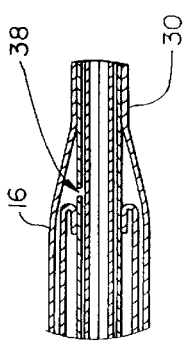
FIG. 2B is a fragment of FIG. 2 showing an alternate L-seal embodiment of the slipping sleeve.

This deployment flexibility can be accomplished in several ways. One version shown in FIG. 1 is the use of separate lumens 32 and 34 for inflating slipping sleeves 14 and 16, through inflation ports 36 and 38, to allow individual control over each sleeve 14 and 16. This is best seen in FIG. 2. Another version is shown best in FIG. 2A, where both the proximal inflation port 36 and the distal inflation port 38 share the same lumen, which allows for a decreased profile. In the shared lumen version, there are several ways to control the movement of sleeves 14 and 16. Sleeves 14 and 16 can be sized differently, as shown in FIG. 1, such that equal sleeve inflation will cause the distal sleeve 16 to release the distal end of stent 17 before the proximal end of stent 17 is released by the proximal sleeve 14. The tightness of seal 30 of each sleeve can be varied as well by controlling the immersion time and temperature in the hot water bath. Also, speed control bumps 42 or ridges can be formed in the catheter 12 (best shown in FIG. 3) to individually control the slipping of each sleeve 14 and 16. The sleeve outer diameter could also be varied, which would vary the movement of the slipping sleeves. Of course, all of the various techniques could be easily combined as well by those skilled in the art.

It should also be noted that although preferred, the water soluble bands are not required in the embodiment of FIG. 1. Sleeves 14 and 16 can optionally be used to contain stent 17 as disclosed in Wallsten 4,732,152; Wallsten 4,848,343 and Imbert 4,875,480. The same means used to cause sleeves 14 and 16 to retract will also permit the stent to self-expand as sleeves 14 and 16 are retracted. It should also be understood that the various techniques of varying the sleeve lengths of sleeves 14 and 16, the tightness of the slipping seal 30, the outside diameter of sleeves 14 and 16, placement of speed control bumps 42 on catheter 12 and individual lumens for each of the sleeves 14 and 16 allow for great control over the movement of sleeves 14 and 16, with or without water soluble band(s) 18, 60 or 62.

Referring now to FIGS. 7–10, yet another embodiment of the stent delivery device is shown in which a single slipping sleeve 70 is shown in the uncovered position (FIG. 7). The distal end of sleeve 70 is contained by cylindrical gripping means 72, which is made of silicone rubber, latex or the like, and is bonded to catheter 12 with an open end oriented toward the sleeve and the stent to receive them as best seen in FIG. 8. The stent 17 may, but need not, extend into gripping means 72 along with sleeve 70. FIG. 8 shows the device in the covered position with the stent 17 confined to its reduced radius delivery configuration. It should be understood that this embodiment, like those disclosed above can optionally use water soluble band(s) 18, 60, 62, a swelling material or other degradable material to confined stent 17, or stent 17 can be held in its reduced delivery configuration by sleeve 70 alone.

An alternate embodiment of the invention of FIGS. 7–10 replaces the cylindrical gripping means 72 with the embodiment shown in FIG. 8A. In this case the gripping means 72 has been replaced with a silicon ball 73 that allows the sleeve to be rolled over it to create a water tight seal. Other materials and shapes can be used that have a desired degree of compliance with the slipping sleeve.

Figure 9:
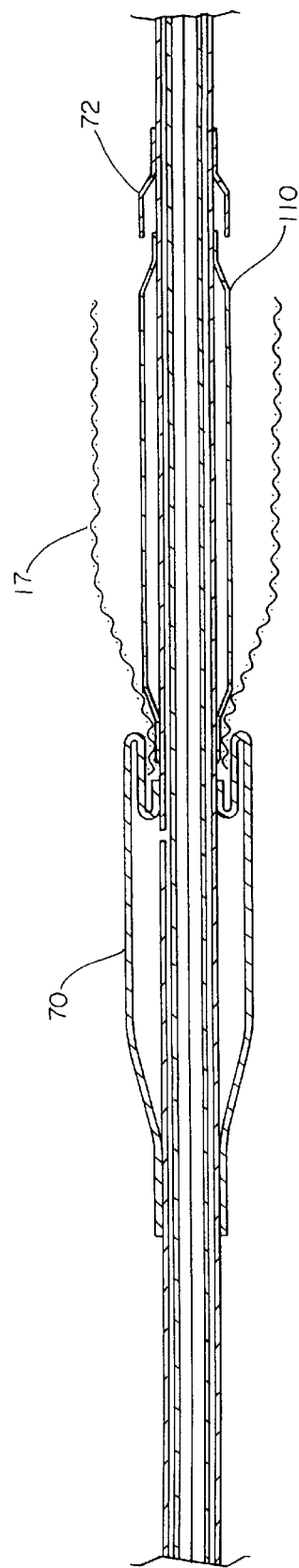
FIG. 9 is a side elevational section of the distal end portion of the invention of FIG. 7 in mid-deployment.

FIG. 9 shows the device in mid-deployment. Retraction of sleeve 70 has pulled stent 17 from gripping means 72 and allowed stent 17 to self-expand as shown.

FIGS. 10A and 10B show a technique for recovering a misplaced stent prior to completely releasing the stent shown in FIG. 9. A guide catheter or other tubular sheath 76 is advanced to surround sleeve 70 and partially deployed stent 17, then the entire assembly is withdrawn from the body lumen.

Referring now to FIG. 11, another embodiment of a stent delivery device is shown which uses push/pull wires to move a pair of sleeves. Catheter 12 can be seen to have three lumens in sectioned view 11A, a center lumen 52 for guide wire 50, a proximal lumen 80 for proximal pull wire 82 and a distal lumen 84 for distal push wire 86. Sectioned view 11B shows that the catheter has a skived cross-section to allow proximal wire 82 to leave the lumen and to attach to proximal sleeve 88. Distal wire 86 leaves its lumen and attaches to distal sleeve 90 at 92. By appropriately pushing on a handle 93 attached to distal push wire 86, and pulling on a handle 95 attached to proximal pull wire 82, the physician can release stent 17. This arrangement also allows control over which end of the stent is released first. Both wires 82 and 86 may be teflon coated to lessen the friction caused by movement in their respective lumens.

Figure 12:
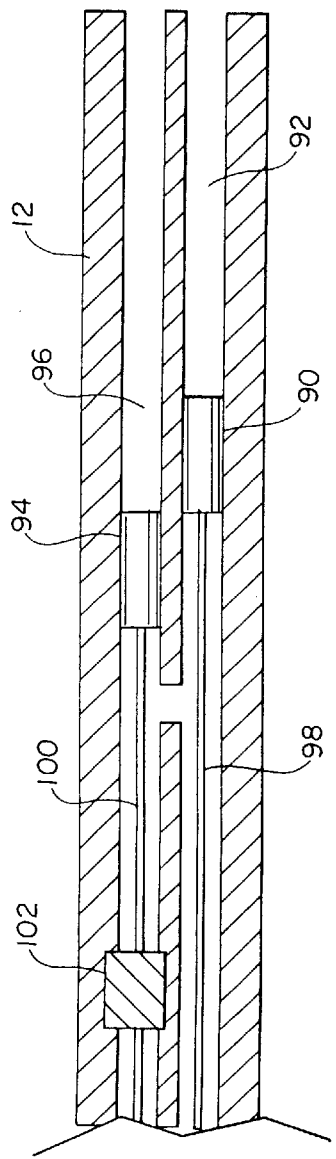
FIG. 12 is a side elevational section of a further embodiment of a stent delivery device utilizing pistons and showing the position of the pistons when the stent is in the confined position.
Figure 13:
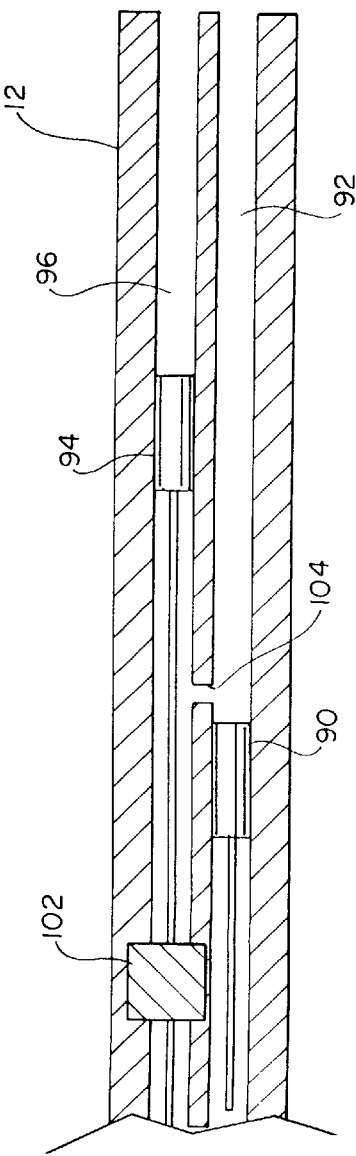
FIG. 13 is a side elevational section of the embodiment of FIG. 12 showing the position of the pistons when in the deployed position.

Referring now to FIGS. 12 and 13, another embodiment of a stent delivery device is shown which uses hydraulic pressure to move a pair of sleeves. FIG. 12 shows catheter 12 proximally of the distal end with a distal piston 90 in lumen 92 and a proximal piston 94 in lumen 96. Wires 98 and 100 extend from the pistons 90 and 94, respectively, to attach to the sleeves 90 and 88 as in the previous embodiment. Wire 100 extends through a fixed seal 102. FIG. 13 shows this embodiment in the deployed position, where fluid pressure in lumen 92 has pushed distal piston distally, thereby pushing distal sleeve 90 distally. Once distal piston is past access port 104 the fluid will enter lumen 96 and force proximal piston proximally in lumen 96, thereby pulling proximal sleeve 88 proximally.

Figure 14:
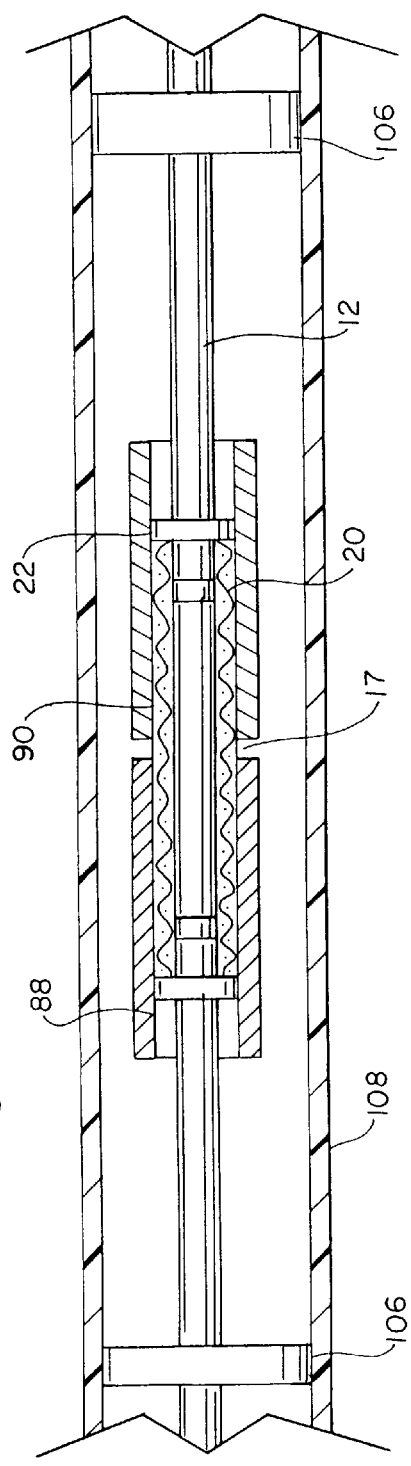
FIG. 14 is a side elevational section of the distal end portion of the embodiments of FIGS. 11 or 12, i.e., a push/pull version or a piston operated version, respectively, the stent being in the confined position.
Figure 15:
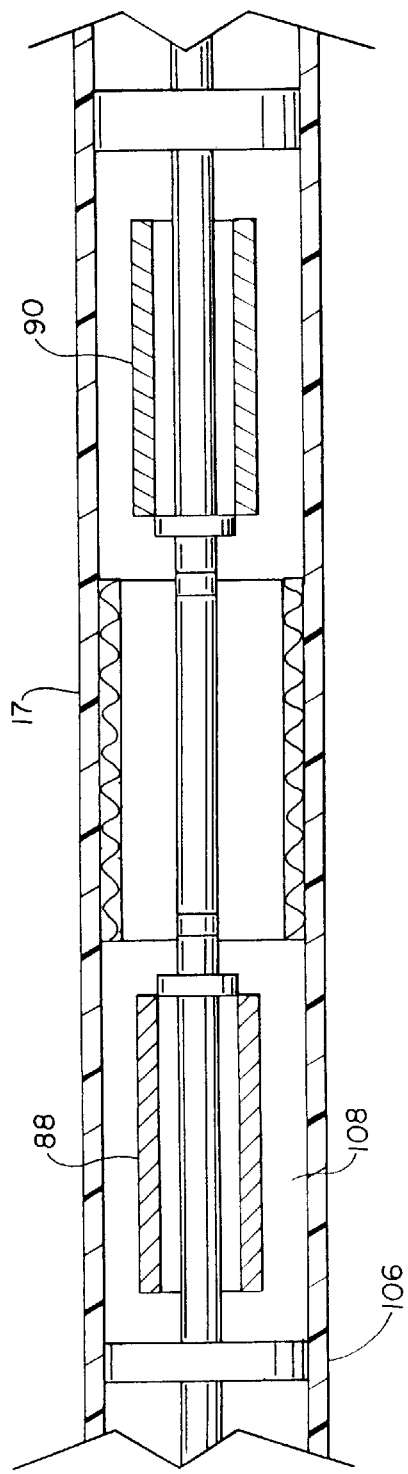
FIG. 15 is a side elevational section of the distal end portion of the embodiments of FIGS. 11 or 12, the stent being in the deployed position.

FIGS. 14 and 15 show the distal end of the catheter for both the previous two embodiments in both the confined and deployed positions. Catheter securing balloons 106 can be optionally inflated prior to deployment to aid in preventing catheter movement during deployment by frictionally engaging vessel wall 108. Balloons 106 are made from a more compliant material such as latex, silicone or the like, and are well known in the art. Catheter securing balloons 106 can be used in connection with any of the embodiments by simply adding the appropriate lumens or access from existing fluid lumens. The catheter can also be secured in the vessel by means of a magnet attached to the proximal end portion of the catheter and guidewire, with the guidewire secured using a magnet external of the body.

Once the stent is deployed using any of the embodiments, a placement balloon 110 (best seen in FIG. 9) can be inflated to seat the stent into the vessel wall, as is well known in the art. It should be understood that the placement balloon, as well as a partially deployed stent, if desired, can be recovered using the push/pull wire embodiment. For the other embodiments, if necessary a guide catheter or sheath can be advanced to retrieve the placement balloon or partially deployed stents.

It has been found that delivering an uncovered stent to a deployment site can damage the vessel wall, due to the sharp edges of the stent. It has also been found that an uncovered stent may move axially along the catheter and may even slide off the catheter. Therefore the inventive delivery system can also advantageously be used to deliver a non self-expanding stent to a deployment site safely since the stent is covered and prevents movement of the stent, relative to the catheter, before deployment. A non self-expanding stent can be deployed by using a placement balloon of the type shown in FIG. 9 (reference 110) to expand stent 17, as is well known in the art.

Figure 16:
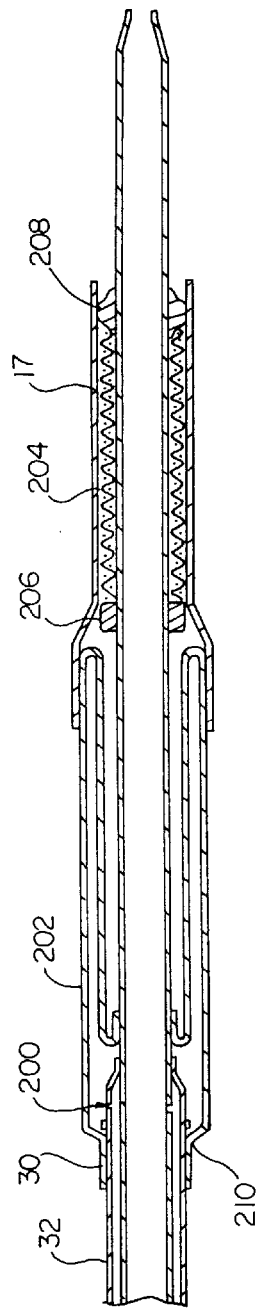
FIG. 16 is a side elevational section showing a single layer sheath alternate embodiment.

Referring now to FIG. 16, a single layer sheath embodiment of the stent delivery device is shown in which reference numeral 32 is a fluid lumen for providing fluid through fluid access port 200 to the slipping sleeve 202. Adhesively attached to the slipping sleeve 202 is the single layer sheath 204 which can retain the stent 17 in its delivery configuration. The stent is secured between stent bumper 206 and fluid tight seal 208. As fluid is pumped through lumen 32 into slipping sleeve 202, the slipping seal 30 moves axially away from the stent 17, retracting the single layer sheath 204 and allowing the stent 17 to self-expand. Stent 17 may optionally be surrounded by a dissolving band or pressed into a swelling band, as discussed above, the band acting to restrain the stent 17 in its delivery configuration. Retraction of the single layer sheath 204 allows fluid access to the dissolving or swelling band, which allows the stent to self-expand in a controlled manner as discussed above. The single layer sheath may be made from the same materials and in the same manner as discussed above in connection with the slipping sleeves.

Figure 17:
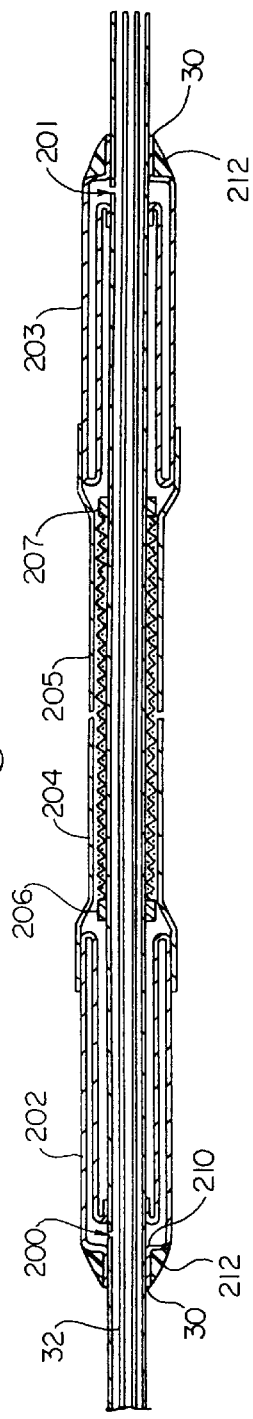
FIG. 17 is a side elevational section showing another embodiment of the single layer sheath stent delivery device.

Referring now to FIG. 17, an alternate embodiment of the single layer sheath stent delivery device is shown in which reference numeral 32 is a shared fluid lumen for providing fluid through fluid access ports 200 and 201 to the slipping sleeves 202 and 203. Separate fluid lumens can also be provided as in FIG. 1 to allow individual control over each slipping sleeve. Adhesively attached to the slipping sleeves 202 and 203 are the single layer sheaths 204 and 205 which can retain the stent 17 in its delivery configuration. The stent 17 is secured between stent bumpers 206 and 207 and the single layer sheaths 204 and 205 may abut to provide a fluid tight seal, if desired. As fluid is pumped through lumen 32 into slipping sleeves 202 and 203, the slipping seals 30 move axially away from the stent 17, retracting the single layer sheaths 204 and 205, allowing the stent 17 to self-expand. Stent 17 may optionally be surrounded by a dissolving band or pressed into a swelling band, as discussed above, the band acting to restrain the stent 17 in its delivery configuration. Retraction of the single layer sheaths 204 and 205 allows fluid access to the dissolving or swelling band, which allows the stent to self-expand in a controlled manner as discussed above.

Applicants' have discovered experimentally that the 45° knee 26 (discussed above) in the slipping sleeve is sometimes weakened due to the forces acting on the 45° section of slip seal 30. Therefore, to provide additional strength, the embodiments of FIGS. 16 or 17 may be formed with 90° knees 210, with the knee filled with a cone shaped adhesive ridge 212 shown in FIG. 17. The adhesive ridge 212 supports the 90° knee 210 and provides a smooth 45° transition zone which more evenly transfers the force to the slip seal 30.

Figure 18:
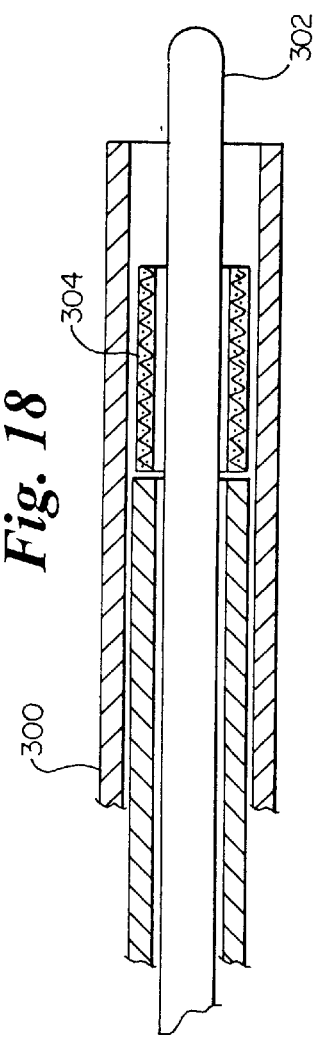
FIG. 18 shows yet another embodiment of the inventive stent delivery device.

Referring now to FIG. 18, an alternate embodiment of the invention is shown in which the self-expanding stent is any self-expanding stent made of a resilient metal or plastic material, which would include shape memory metal stents such as nitinol stents, which are well known in the art. The self-expanding stent is retained in its reduced delivery radius using a collagen sleeve, liner or both.

Applicants have a copending application entitled "IMPROVED TISSUE SUPPORTING DEVICES" filed May 19, 1994 as Ser. No. 08/246,320 which discloses a preferred stent. The entire contents of Ser. No. 08/246,320 are hereby incorporated by reference. The stents described in this application are generally cylindrical or tubular in overall shape and of such a configuration as to allow radial expansion for enlargement. Furthermore, the stents are comprised of at least one component which exhibits a resiliency or spring-like tendency to self-expand the device and at least one other component which is deformable so as to allow an external force, such as a balloon positioned within the body of the device, to further expand it to a final desired size. Preferably, the stents are made of metal and most preferably of shape memory alloys.

In its broader concept, the device, such as a stent of Ser. No. 08/246,320 is made of a first component which is a resilient spring-like metal for self-expansion and the second component is a deformable metal for final sizing. In the more preferred shape memory embodiment, the first component is a self-expanding austenitic one and second is an martensitic one capable of deformation.

The most preferred embodiment the device described in 08/246,320 is a stent, preferably of shape memory alloy. The most preferred shape memory alloy is Ni-Ti, although any of the other known shape memory alloys may be used as well. Such other alloys include: Au-Cd, Cu-Zn, In-Ti, Cu-Zn-Al, Ti-Nb, Au-Cu-Zn, Cu-Zn-Sn, Cu-Zn-Si, Cu-Al-Ni, Ag-Cd, Cu-Sn, Cu-Zn-Ga, Ni-Al, Fe-Pt, U-Nb, Ti-Pd-Ni, Fe-Mn-Si, and the like. These alloys may also be doped with small amounts of other elements for various property modifications as may be desired and known in the art.

The stent used in connection with any of the embodiments described herein is preferably the two component stent described above. However, a typical memory metal self-expanding stent, such as a nitinol stent, may also be used. Any type of self-expanding stent, whether made of a resilient metal or plastic material, may be used. The term nitinol is intended to refer to the two component memory metal stent discussed above as well as any other type of known memory metal stent.

Applicants have found that in delivering a self-expanding stent, such as the preferred two component nitinol stent described above, as the stent is moved through the body carried by the catheter, the body temperature of the patient may heat the nitinol stent to its transition temperature, causing it to self-expand. This is considered undesirable because it can exert an outward force on the various sheaths discussed above in connection with FIGS. 1–18 which prevent fluid from hydrating the stent.

It is also known to insert a stent at the proximal end of the catheter, and push the stent through a lumen inside the catheter and out the distal end of the catheter at the deployment site. Such a device is disclosed for example in European Patent Application EP 0 556 850 A1, published Aug. 25, 1993. As the stent is moving through the lumen of the catheter, the body temperature of the patient may heat the nitinol stent to its transition temperature, causing it to self-expand. This can increase the frictional engagement of the stent with the lumen of the catheter, making it difficult to push down the length of the catheter to the delivery site at the distal end.

Applicants overcome this problem by surrounding the stent with an outer sleeve of water swelling material, such as collagen, lining the inside of the stent with a swelling material, or both. This alternate embodiment may be used in connection with the various embodiments discussed above in connection with FIGS. 1–17 to eliminate the outward self-expanding force exerted by an type of memory metal stent after it has reached its transition temperature.

Referring now to FIG. 18, the water swelling sleeve and/or liner discussed above is shown in a stent pusher embodiment. The catheter is referred to generally at 300 and the guidewire at 302. The self-expanding stent, including its collagen sleeve, liner or both is shown generally at 304, axially surrounding the guidewire. Stent pusher 306 is used to push the stent through the lumen of catheter 300 and out the distal end of the catheter to the delivery site. In the preferred embodiment, the water swelling material is formulated so that it is slow to hydrate to allow sufficient time to deliver the stent to the deployment site. Alternatively, a means could be included which would prevent the stent from being hydrated until the collagen sleeve and/or lined stent was delivered to its deployment site.

The stent can be surrounded by an outer sleeve of water swelling material, which in this embodiment is preferably collagen. The stent can optionally also be held in its reduced delivery configuration by a liner of collagen which is inside the stent. Finally, the stent can optionally use both the outer sleeve and the inner liner.

The collagen sleeve may be of collagen per se or it may be carried on a support such as DACRON® fabric or the like as is known and disclosed for example in U.S. Pat. Nos. 5,256,418, 5,201,764 and 5,197,977, the entire content of which are all incorporated herein by reference, particularly those portions which relate to the formation of collagen tubes. The support may be a fabric, woven or braided, and may also be of polyester, polyethylene, polyurethane or PTFE. The term "collagen material" is used herein to refer to both supported and unsupported collagen for the sleeve element of this invention.

The preferred collagen at present appears to be intestinal collagen believed to be of Type I and Type IV, and in particular a collagen known as Small Intestine Submucosa (SIS) which has particular use herein, alone and in combination with other collagen material such as Type I. SIS is predominantly a Type IV material. It is described in detail in U.S. Pat. Nos. 4,902,508; 4,956,178 and 5,281,422, all of which are incorporated herein by reference. In addition to SIS, with or without Type I, the collagen may also be made of Type III or Type IV or combinations thereof. U.S. Pat. Nos. 4,950,483, 5,110,064 and 5,024,841 relate to collagen productions and are incorporated herein by reference. Collagen can be extracted from various structural tissues as is known in the art and reformed into sheets or tubes and attached to a fully expanded stent, by for example, wrapping the stent with the collagen and attaching the collagen to itself or by weaving the collagen through the openings in the stent and attaching it to itself. The stent is then mechanically pulled down to its reduced diameter and the collagen is dried, which holds the stent in its reduced diameter. The collagen may also be dried onto the unexpanded stents mentioned above.

As such, stent sleeves and/or liners constructed of these materials can be used for reservoirs for pharmaceutical agents and the like. Hydrophilic drugs such as heparin or hirudin to protect against coagulation or hydrophobic drugs such as prostaglandins or aspirin and vitamin E may be used to protect against platelet activation. Vitamin E and other anti oxidants such as sodium ascorbate, phendies, carbazoles, and tocotrienols may be used to protect against oxidation. Most preferably, the collagen material will include a quantity of drug material such as heparin which may be incorporated into the collagen in known manner for release after placement of the stent. Generally, the drug materials may include the known antithrombic agents, antibacterial and/or antimicrobial agents, antifungal agents and the like.

During the formation process of the sleeve or liner, various components may be added to the solution prior to drying or may be added separately after formation of the device. Heparin could be directly added to the forming solution as could aspirin. Benzalkonium heparin, a modified form of heparin which makes it more hydrophobic could be used to coat the formed device or film from a solution of alcohol. Prostaglandins PGI2 or PGE2 may be added from a solution of propanol or propanol/methylene chloride onto a collagen sleeve formed from an aqueous base. Vitamin E could be added from even less polar solutions as chloroform. Other agents could be similarly added. The term "agents" is used herein to include all such additives.

Cells of the blood vessel wall synthesize and secrete several kinds of macromolecules forming extracellular matrix. The components of this matrix comprise several large proteins that may be synthetically constructed to form films, tubes or multilayer sheets or other constructs. Among these biological components are collagens of several types, elastin, glycosaminoglycans (GAGS), fibronectin and laminin. Collagens are three chain glycoproteins with molecular weights of about 300,000. Elastin is an insoluble nonpolar amino acid rich crosslinked protein. The GAGs are linear chain polysaccharides with various negative charges with various molecular weights ranging from thousands to millions. Included in the GAGs are heparin and heparin sulfate, dermatin sulfate and chondroitin sulfate. Fibronectin is a 440,000 MW 2-chain adhesive glycoprotein that acts as a substrate for many cell types and in cell-cell interactions. Laminin is a 2 chain glycoprotein of MW about 850,000 and acts as a basement membrane structure for cellular-molecular interactions. Each of these macromolecules may be combined in a multitude of combinations to form composites. These are all natural materials that serve specific functions and are exposed to blood under normal repair conditions. It is therefore expected that, if a covering sleeve for a stent were made of these macromolecules and used in the course of intervention, repair of a blood vessel would proceed more naturally than if a similar device were constructed of synthetic polymers such as polyethylene, polyteraphthalate or polyurethanes. Macromolecules are also referred to herein generally as "collagen". In this patent collagen thus refers to not only the specific class of macromolecules known as collagen but those natural materials that normally or naturally form membranes with collagen as laminin, glycosaminoglycans, proteoglycans, pure carbohydrates, fibrin, fibronectin, hyaluronic acid or the like, and other natural materials that come into contact with collagen that could be made into film as albumin, globulins, and other blood borne proteins. Tubular films made from any combination of the above materials could provide substantially the same purpose as that of pure collagen.

The collagen sleeve/liner discussed above could also be used with the embodiments disclosed above in connection with FIGS. 1–17. For example, the retractable sheath 66 discussed above in connection with FIG. 6 could prevent fluid access to the collagen material until a wire is used to retract the sheath 66, allowing fluid to access the collagen material, allowing it to swell.

It should also be understood, that the collagen material remains in the body, whether as a sleeve surrounding the stent, a liner inside the stent or both, to aid forming of a non-thrombogenic cushion for the stent in the vascular lumen as well as a natural substrate for endotheliazation. It should also be understood that the dissolving band embodiments discussed above could also be used as an alternative to the swelling band material such as collagen, but are not preferred since they do not remain behind as a non-thrombogenic agent.

This completes the description of the preferred and alternate embodiments of the invention. It is to be understood that even though numerous characteristics and advantages of the present invention have been set forth in the foregoing description, together with the details of the structure and function of the invention, the disclosure is illustrative only and changes may be made in detail, especially in matters of shape, size and arrangement of parts within the principals of the invention, to the full extent indicated by the broad, general meaning of the terms in which the appended claims are expressed. Those skilled in the art may recognize other equivalents to the specific embodiment described herein which are intended to be encompassed by the claims attached hereto.

What is claimed is:

1. A stent delivery system for implantation of a stent in a vessel comprising:

an elongate flexible catheter having proximal and distal ends;

a stent having proximal and distal ends, the stent surrounding the flexible catheter near its distal end, the stent being in a delivery configuration where the stent has a reduced radius along its entire axial length;

a retractable sheath for retaining the stent in the delivery configuration and for deploying the stent, the sheath holding the self-expanding stent in its delivery configuration against the outwardly urging force of the self-expanding stent;

a retraction device for retracting the retractable sheath, the retraction device comprising a piston housing and a piston contained therein, the piston actatable by pressurized fluid supplied to at least a portion of the piston housing by an inflation lumen, the retraction device further comprising a connecting member, one end of which connects to the retractable sheath, the other end of the connecting member connecting to the piston, whereby the retractable sheath may be retracted by supplying a fluid under pressure to the inflation lumen so as to displace the piston, the piston in turn displacing the retractable sheath so as to expose at least a portion of the stent.

2. The stent delivery system of claim 1 wherein the connecting member comprises a wire.

3. The stent delivery system of claim 1 wherein the piston housing is sealed at one end.

4. The stent delivery system of claim 1 wherein the piston housing is coaxial with the catheter.

5. The stent delivery system of claim 1 wherein the stent is self-expandable.

6. The stent delivery system of claim 1 having only one piston actuatable by pressurized fluid.

7. The stent delivery system of claim 1 further comprising a second retractable sheath for retaining the stent in the delivery configuration and for deploying the stent, the second sheath holding the self-expanding stent in its delivery configuration against the outwardly urging force of the self-expanding stent;

a second retraction device for retracting the second retractable sheath, the second retraction device comprising a second piston housing and a second piston contained therein, the second piston actuatable by a pressurized fluid supplied to at least a portion of the second piston housing from the first piston housing, the second retraction device further comprising a second connecting member, one end of which connects to the second retractable sheath, the other end of the second connecting member connecting to the second piston.

8. The stent delivery system of claim 7 wherein the second connecting member comprises a wire.

9. The stent delivery system of claim 7 wherein the first and second pistons move in opposing directions on retraction of the first and second retractable sheaths.

10. The stent delivery system of claim 7 wherein the stent is self-expandable.

11. A method for delivering a stent to a desired location in a bodily lumen using the stent delivery system of claim 1 comprising the steps of:

providing a stent delivery system as in claim 1;

inserting at least a portion of the stent delivery system in a bodily vessel;

advancing the stent to a desired bodily location;

providing a source of fluid;

supplying the fluid under pressure to the housing so as to actuate the piston and retract the sheath;

deploying the stent;

withdrawing the stent delivery system from the bodily vessel.

12. A medical device delivery system for delivering a medical device to a desired location in a bodily lumen comprising an elongate flexible catheter having proximal and distal ends, the catheter having a medical device mounting region near its distal end for mounting thereon a medical device;

a retractable sheath covering the medical device mounting region;

a retraction device for retracting the retractable sheath, the retraction device comprising a piston housing and a piston contained therein, the piston in fluid communication with an inflation lumen, a connecting member, one end of which connects to the retractable sheath, the other end of the connecting member connecting to the piston, whereby the retractable sheath may be retracted by supplying a fluid under pressure to the inflation lumen so as to displace the piston, the piston in turn displacing the retractable sheath from its position over the medical device mounting region.

13. The medical device delivery system of claim 12 wherein the medical device is a stent and the stent is mounted on the medical device mounting region of the catheter.

14. The medical device delivery system of claim 13 wherein the stent is self-expandable.

15. A method for delivering a medical device to a desired location in a bodily lumen using the apparatus of claim 12 comprising the steps of:

providing a medical device delivery system as in claim 12;

providing a medical device for placement about the medical device mounting region;

placing the medical device about the medical device mounting region of the medical device delivery system and covering the medical device with the retractable sheath;

inserting at least a portion of the medical device delivery apparatus in a bodily vessel;

advancing the medical device to a desired bodily location;

providing a source of fluid;

supplying the fluid under pressure to the first housing so as to actuate the piston and retract the sheath;

deploying the medical device;

withdrawing the medical device delivery apparatus from the bodily vessel.

16. The method of claim 15 wherein the medical device is a stent.

\* \* \* \* \*